(12) United States Patent
Oku et al.

(10) Patent No.: US 6,620,951 B2
(45) Date of Patent: Sep. 16, 2003

(54) PROCESS FOR PRODUCING OXIRANE COMPOUND

(75) Inventors: Noriaki Oku, Ichihara (JP); Masaaki Katao, Ichihara (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/221,374

(22) PCT Filed: Mar. 19, 2001

(86) PCT No.: PCT/JP01/02189

§ 371 (c)(1),
(2), (4) Date: Sep. 12, 2002

(87) PCT Pub. No.: WO01/70713

PCT Pub. Date: Sep. 27, 2001

(65) Prior Publication Data

US 2003/0097009 A1 May 22, 2003

(30) Foreign Application Priority Data

Mar. 24, 2000 (JP) .................................... 2000-083954

(51) Int. Cl.$^7$ ............................................. C07D 301/19
(52) U.S. Cl. ....................................... 549/529; 549/530
(58) Field of Search ................................. 549/529, 530

(56) References Cited

U.S. PATENT DOCUMENTS

| 5,410,077 A | 4/1995 | Wu et al. |
| 5,760,253 A | 6/1998 | Danner et al. |
| 5,840,933 A | 11/1998 | Jubin, Jr. et al. |
| 5,849,937 A | 12/1998 | Jubin, Jr. et al. |

*Primary Examiner*—Ba K. Trinh
(74) *Attorney, Agent, or Firm*—Sughrue Mion, PLLC

(57) ABSTRACT

A process for producing an oxirane compound from an organic peroxide other than ethylbenzene hydroperoxide and an olefin in the presence of an immobilized catalyst bed, wherein the process satisfies the following conditions (1) to (4):

(1) the catalyst bed is divided into n catalyst beds and the catalyst beds are used in series, wherein n is an integer of 2 or more, (2) a fresh organic peroxide is divided into portions, which are supplied to respective inlets of the catalyst beds, (3) a fresh olefin is supplied to the inlet of the first catalyst bed, and (4) the reaction mixture discharged from each outlet of respective catalyst beds excluding the final catalyst bed is supplied to the inlet of the subsequent catalyst bed.

2 Claims, 2 Drawing Sheets n catalyst beds n catalyst beds

PROCESS FOR PRODUCING OXIRANE COMPOUND

This application is a 371 of PCT/JP01/02189 filed on Mar. 19, 2001.

TECHNICAL FIELD

The present invention relates to a process for producing an oxirane compound. More particularly, the invention relates to a process for producing an oxirane compound from an organic peroxide other than ethylbenzene hydroperoxide and an olefin in the presence of an immobilized catalyst bed, wherein said process for producing an oxirane compound has excellent characteristics that it can prevent a runaway of a reaction accompanied with generation of heat and can be stably carried out with a high yield.

BACKGROUND ART

Techniques for producing an oxirane compound from an organic peroxide and an olefin in the presence of an immobilized catalyst bed have been publicly known. Since the reaction producing an oxirane compound from an organic peroxide and an olefin is an exothermic reaction, there have been problems that the reaction accompanies a sudden generation of heat in the immobilized catalyst bed, thereby making difficult a stable run, and sometimes not only the catalyst is deteriorated but also the yield is lowered.

DISCLOSURE OF THE INVENTION

An object of the present invention is to provide a process for producing an oxirane compound from an organic peroxide other than ethylbenzene hydroperoxide and an olefin in the presence of an immobilized catalyst bed, wherein said process for producing an oxirane compound has excellent characteristics that it can prevent a run away of a reaction accompanied with generation of heat and can be stably carried out with a high yield.

Namely, the present invention relates to a process for producing an oxirane compound from an organic peroxide other than ethylbenzene hydroperoxide and an olefin in the presence of an immobilized catalyst bed, wherein the process satisfies the following conditions (1) to (4):

(1) the catalyst bed is divided into n catalyst beds and the catalyst beds are used in series, wherein n is an integer of 2 or more, (2) a fresh organic peroxide is divided into portions, which are supplied to respective inlets of the catalyst beds, (3) a fresh olefin is supplied to the inlet of the first catalyst bed, and (4) the reaction mixture discharged from each outlet of respective catalyst beds excluding the final catalyst bed is supplied to the inlet of the subsequent catalyst bed.

1. catalyst bed,
2. fresh organic peroxide,
3. fresh olefin,
4. cooling equipment

BEST MODE FOR CARRYING OUT THE INVENTION

As the organic peroxide other than ethylbenzene hydroperoxide used in the present invention, organic peroxides such as tert-butyl hydroperoxide, isopropylbenzene hydroperoxide and the like, can be exemplified.

As the olefin used in the present invention, olefins having 3–8 carbons such as propylene, hexene, octene and the like can be exemplified. For example, when isopropylbenzene hydroperoxide is used as the organic peroxide other than ethylbenzene hydroperoxide and propylene is used as the olefin, propylene oxide is obtained as the oxirane compound.

The catalyst used in the present invention can include a titanium-containing silicon oxide catalyst and the like. Among them, a titanium-containing silicon oxide catalyst is preferred from the viewpoint that it allows attainment of a high yield and a high selectivity.

The process for production according to the present invention satisfies the following conditions (1) to (4):

(1) the catalyst bed is divided into n catalyst beds and the catalyst beds are used in series, wherein n is an integer of 2 or more, (2) a fresh organic peroxide other than ethylbenzene hydroperoxide is divided into portions, which are supplied to respective inlets of the catalyst beds, (3) a fresh olefin is supplied to the inlet of the first catalyst bed, and (4) the reaction mixture discharged from each outlet of respective catalyst beds excluding the final catalyst bed is supplied to the inlet of the subsequent catalyst bed.

The condition (1) is to divide the catalyst bed into n beds and use them in series. The expression "use in series" means a connection of catalyst beds in which a reaction mixture from an outlet of a certain divided catalyst bed is supplied to an inlet of the subsequent catalyst bed and finally a reaction mixture is obtained from an outlet of the n-th catalyst bed. Additionally, n is an integer of 2 or larger and is usually 2 to 20. Methods for dividing the catalyst bed for distributing the heat of reaction include a method in which independently placed n reactors containing the catalyst are used (FIG. 1), a method in which catalyst beds are placed in partitions in one reactor (FIG. 2) and the like. The divided catalyst beds may be the same or different in the kind or amount of the catalyst charged.

Figure 1:
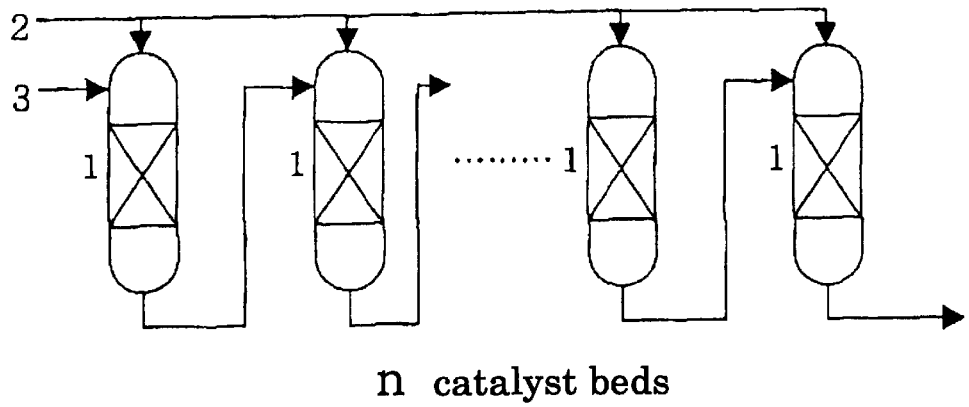
FIGS. 1 to 3 show examples of embodiments for practicing the invention.
Figure 2:
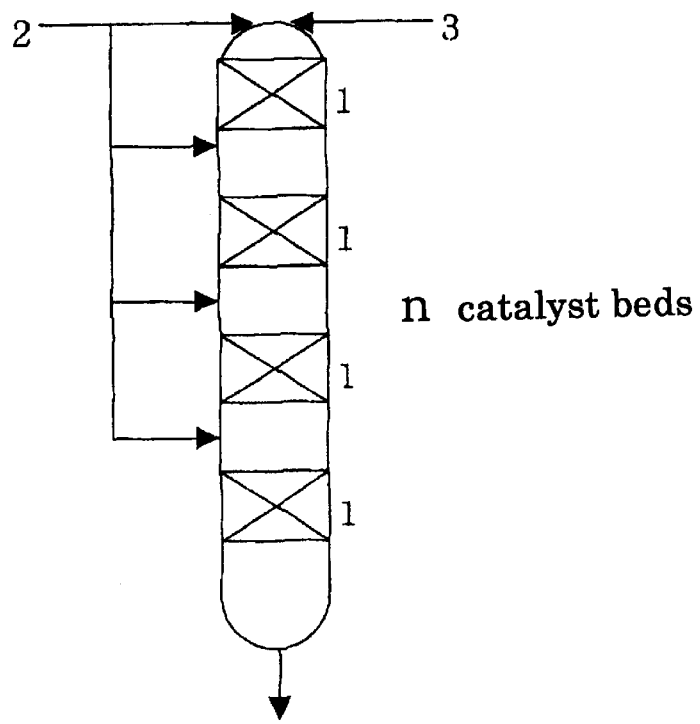

The condition (2) is to divide and supply the fresh organic peroxide to respective inlets of the catalyst beds (see FIG. 1 and FIG. 2). The term fresh organic peroxide means an organic peroxide supplied from outside of the system constituted according to the invention.

The condition (3) is to supply an fresh olefin to an inlet of the first catalyst bed (see FIG. 1 and FIG. 2). The term fresh olefin means an olefin supplied from outside of the system constituted according to the invention. It is preferred that the total amount of the fresh olefin is supplied to an inlet of the first catalyst bed, but a part of the fresh olefin may be divided and supplied to other place(s) than the inlet of the first catalyst bed insofar as the effect of the present invention is not deteriorated.

The condition (4) is to supply the reaction mixture discharged from each outlet of respective catalyst beds excluding the final catalyst bed to the inlet of the subsequent catalyst bed (see FIG. 1 and FIG. 2). In other words, the reaction mixture discharged from an outlet of a catalyst bed serially passes through catalyst bed(s) in order. A part of the reaction mixture discharged from an outlet of a catalyst bed may be recycled to the inlet of the same catalyst bed insofar as the effect of the invention is not deteriorated. This is effective for preventing a rise in temperature caused by the heat of reaction in the catalyst bed.

By satisfying the above-described conditions, the present invention realizes the effect that a runaway of reaction accompanied by generation of heat can be prevented and an oxirane compound can be stably produced with high yield. In other words, it allows suppression of lowering in the catalyst activity by thermal deterioration, shortening of the catalyst life, lowering in the yield, runaway of the reaction and the like due to generation of heat accompanied by the reaction of the organic peroxide and an olefin. Since the epoxidation reaction between the organic peroxide and an olefin generates very abundant heat and is highly temperature-dependent, the reaction has high danger of reaction runaway. Generally, the amount of reaction has been adjusted by controlling the temperature at the inlet of the catalyst bed or by compulsorily removing heat from the outside. However, it has become difficult to set the reaction temperature with accuracy according to the activity of a specific catalyst owing to a change in the catalyst activity with time or difference in time between the outlet and the inlet of the reactor, and therefore, not only problems arises that the activity of the catalyst is lowered and the yield decreases due to sudden increase in the amount of reaction and outflow of unreacted organic peroxide, but also there is a problem in stable operation. According to the present invention, the rise in temperature by the heat of the reaction can be controlled by partitioning the catalyst bed and adjusting feeding amount to respective catalyst beds; therefore, it becomes possible to prevent lowering in the catalyst activity and decrease in the yield accompanied by sudden rise in temperature in the catalyst bed, and additionally, the runaway of the reaction by a rise in the reaction temperature. In the present invention, a heat-removing apparatus such as a heat exchanger may be equipped between catalyst beds. This allows control of the temperature at the inlet of each catalyst bed, and together with the control of feeding amount of the organic peroxide, provides double-safety and stability operation.

Furthermore, a catalyst bed without a feed of the fresh organic peroxide may be placed subsequent to the last divided catalyst bed. This is effective for treating an unreacted organic peroxide in the reaction mixture discharged from the outlet of the last catalyst bed.

The epoxidation temperature is generally 0 to 200° C. and preferably 25 to 200° C. The pressure may be any pressure sufficient to keep liquid state of the reaction mixture. Generally, the pressure is advantageously 100 to 10,000 kPa. The amount of the olefin fed is 1 to 100 times, preferably 3 to 50 times, more preferably 5 to 20 times, based on the total molar number of the organic peroxide fed to catalyst beds. Usually, unreacted olefin is recycled after separation and purification and used as the raw material for the epoxidation reaction.

In a specific example of the reaction, a case wherein propylene oxide is produced from propylene and isopropylbenzene hydroperoxide is described below. The reaction can be carried out in a liquid phase using a solvent. The solvent is a liquid at the temperature and the pressure of the reaction and must be substantially inert to the reactants and the product. The solvent may be composed of a substance existing in a solution of isopropylbenzene hydroperoxide actually used. Usually, the concentration of isopropylbenzene hydroperoxide is 5 to 50% by weight and preferably 10 to 40% by weight. When, for example, it is a mixture with isopropylbenzene as the raw material, said material may be used for a solvent without adding a solvent in particular. Other useful solvents include monocyclic aromatic compounds (e.g. benzene, toluene, chlorobenzene, o-dichlorobenzene), alkanes (e.g. octane, decane, dodecane) and the like. When a titanium-containing silicon compound catalyst is used as the catalyst, propylene oxide is obtained at a reaction pressure of 1 to 10 MPa and a reaction temperature of 50 to 150° C. with a feed of 1 to 20 times by mole of propylene based on the molar amount of fresh isopropylbenzene hydroperoxide fed. Unreacted propylene is recycled to the epoxidation step after separation and purification, and reused.

EXAMPLES

Example 1

Figure 3:
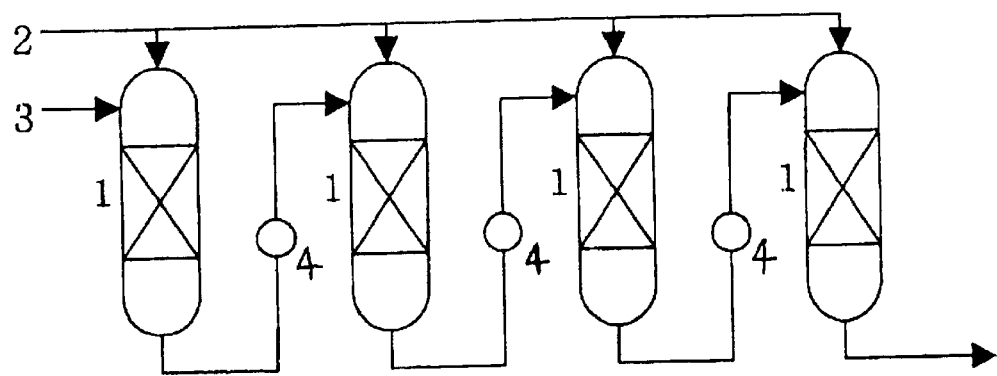

Referring to FIG. 3, each 2 g and total 8 g of Ti-containing silicon oxide catalyst is charged in a fixed-bed flow reactor composed of four independent catalyst beds, and 10 g/hour of a solution containing 25% by weight of isopropylbenzene hydroperoxide is fed in 2.5 g/hour portions to the four catalyst beds. On the other hand, 9 g/hour of propylene is fed to the first catalyst bed. The reaction mixture discharged from the outlet of the first catalyst bed is cooled by a cooling equipment, and the total amount is fed to the second catalyst bed together with the divided 2.5 g/hour amount of the fresh isopropylbenzene hydroperoxide raw material. The reaction mixture discharged from the outlet of the second catalyst bed is cooled, and the total amount is fed to the third catalyst bed together with the divided fresh isopropylbenzene hydroperoxide raw material. The reaction mixture discharged from the outlet of the third catalyst bed is cooled, and the total amount is fed to the fourth catalyst bed together with the divided fresh isopropylbenzene hydroperoxide raw material. The pressure at the respective catalyst beds is adjusted to 7.0 MPa, and the temperature at the inlet of the respective catalyst beds is adjusted such that the conversion of the fed isopropylbenzene hydroperoxide becomes 99%. The results of reaction in this case are shown in Table 1.

Comparative Example 1

Figure 4:
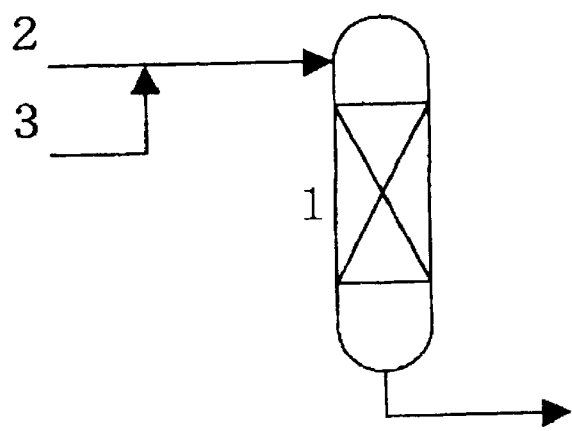
FIG. 4 shows an embodiment according to Comparative Example 1.

Referring to FIG. 4, 8 g of the same catalyst as that in Example 1 is charged in a single catalyst bed, and 10 g/hour of the same solution as that in Example 1 containing 25% by weight of isopropylbenzene hydroperoxide and 9 g/hour of the same propylene as that in Example 1 are fed thereto. The pressure at the catalyst bed is adjusted to 7.0 MPa, and the temperature at the inlet of the catalyst bed is adjusted such that the conversion of the fed isopropylbenzene hydroperoxide becomes 99%. The results of reaction in this case are shown in Table 2, indicating that the yield of propylene decreases and produced amount of acetophenone and phenol formed by thermal decomposition of isopropylbenzene hydroperoxide increases.

TABLE 1

|  | First catalyst bed | Second catalyst bed | Third catalyst bed | Fourth catalyst bed | Total |
|---|---|---|---|---|---|
| Conversion of CHP (%) | 99 | 99 | 99 | 99 | 99 |
| Yield of PO/C3' (%) | 97 | 97 | 97 | 97 | 97 |
| ACP/CHP | 1 | 1 | 1 | 1 | 1 |

TABLE 1-continued

|  | First catalyst bed | Second catalyst bed | Third catalyst bed | Fourth catalyst bed | Total |
|---|---|---|---|---|---|
| PNL/CHP (%) | 0.5 | 0.5 | 0.5 | 0.5 | 0.5 |

TABLE 2

|  | Total |
|---|---|
| Conversion of CHP (%) | 99 |
| Yield of PO/C3' (%) | 90 |
| ACP/CHP (%) | 10 |
| PNL/CHP (%) | 5 |

[Description for Tables]
CHP: Isopropylbenzene hydroperoxide
PO: Propylene oxide
C3': Propylene
ACP: Acetophenone
PNL: Phenol
Conversion of CHP: [Reacted CHP/Supplied CHP] × 100 (%)
Yield of PO/C3': [Produced PO (mol)/Reacted C3' (mol)] × 100 (%)
ACP/CHP: [Produced ACP (mol)/Reacted CHP (mol)] × 100 (%)
PNL/CHP: [Produced PNL (mol)/Reacted CHP (mol)] × 100 (%)

INDUSTRIAL APPLICABILITY

As described above, according to the present invention, a process for producing an oxirane compound from an organic peroxide other than ethylbenzene hydroperoxide and an olefin in the presence of immobilized catalyst beds, said process for producing an oxirane compound having excellent characteristics that it can prevent a runaway of reaction accompanied by generation of heat and can be stably carried out with high yield, can be provided.

What is claimed is:

1. A process for producing an oxirane compound from an organic peroxide other than ethylbenzene hydroperoxide and an olefin in the presence of an immobilized catalyst bed, wherein the process satisfies the following conditions (1) to (4):

(1) the catalyst bed is divided into n catalyst beds and the catalyst beds are used in series, wherein n is an integer of 2 or more, (2) a fresh organic peroxide is divided into portions, which are supplied to respective inlets of the catalyst beds, (3) a fresh olefin is supplied to the inlet of the first catalyst bed, and (4) the reaction mixture discharged from each outlet of respective catalyst beds excluding the final catalyst bed is supplied to the inlet of the subsequent catalyst bed.

2. The process according to claim 1, wherein the catalyst is a titanium-containing silicon oxide catalyst.

* * * * *